(12) United States Patent
Gormley

(10) Patent No.: US 12,410,426 B2
(45) Date of Patent: Sep. 9, 2025

(54) METHODS FOR GENERATING, AND SEQUENCING FROM, ASYMMETRIC ADAPTORS ON THE ENDS OF POLYNUCLEOTIDE TEMPLATES COMPRISING HAIRPIN LOOPS

(71) Applicant: Illumina Cambridge Limited, Cambridge (GB)

(72) Inventor: Niall Anthony Gormley, Cambridge (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 554 days.

(21) Appl. No.: 17/600,046

(22) PCT Filed: Oct. 23, 2020

(86) PCT No.: PCT/EP2020/079902
§ 371 (c)(1),
(2) Date: Sep. 29, 2021

(87) PCT Pub. No.: WO2021/078947
PCT Pub. Date: Apr. 29, 2021

(65) Prior Publication Data
US 2022/0259587 A1    Aug. 18, 2022

Related U.S. Application Data

(60) Provisional application No. 62/926,360, filed on Oct. 25, 2019.

(51) Int. Cl.
*C12Q 1/6806*    (2018.01)
*C12N 15/10*    (2006.01)
*C12Q 1/6869*    (2018.01)

(52) U.S. Cl.
CPC ....... *C12N 15/1093* (2013.01); *C12Q 1/6806* (2013.01); *C12Q 1/6869* (2013.01)

(58) Field of Classification Search
CPC ................ C12Q 1/6806; C12Q 1/6869; C12Q 2525/191; C12Q 2525/301
See application file for complete search history.

(56) References Cited

U.S. PATENT DOCUMENTS

| | | | | |
|---|---|---|---|---|
| 2008/0242560 A1* | 10/2008 | Gunderson | ............ | C12Q 1/682 506/26 |
| 2017/0362639 A1* | 12/2017 | Wilson | ................ | C12Q 1/6858 |
| 2018/0201924 A1 | 7/2018 | Peter et al. | | |

FOREIGN PATENT DOCUMENTS

| | | | | |
|---|---|---|---|---|
| EP | 2692870 A1 * | 2/2014 | .......... | C12Q 1/6816 |
| JP | 2017-512071 A | 5/2017 | | |
| RU | 2017131622 A | 3/2019 | | |
| WO | 2015/104302 A1 | 7/2015 | | |
| WO | 2018/015365 A1 | 1/2018 | | |
| WO | 2018/033730 A1 | 2/2018 | | |
| WO | 2019/006269 A1 | 1/2019 | | |
| WO | 2019/121842 A1 | 6/2019 | | |

OTHER PUBLICATIONS

Bauer et al., "Comparative analysis of the end-joining activity of several DNA ligases," PLoS One, vol. 12, pp. 1-20. (Year: 2017).*
Pan et al., "A novel whole genome amplification method using type IIS restriction enzymes to create overhangs with random sequences," Journal of Biotechnology, vol. 184, pp. 1-6. (Year: 2014).*
Deneke et al., "The protelomerase of temperate *Escherischia coli* phage N15 has cleaving-joining activity," PNAS, vol. 97, No. 14, pp. 7721-7726. (Year: 2000).*
Lindner, Nora, International Preliminary Report on Patentability and Written Opinion, PCT/EP2020/079902, The International Bureau of WIPO, May 5, 2022.
Smirnova, E.A., Office Action and Search Report, Russian Patent Office, Application No. 2021128027, Mar. 6, 2024.
Tanaka, Harue, Office Action, Japan Patent Office, Application No. 2021-558491, Oct. 2, 2024.
Tilkorn, A., International Search Report and Written Opinion, PCT/EP2020/079902, International Searching Authority, European Patent Office, Feb. 3, 2021.

* cited by examiner

*Primary Examiner* — Young J Kim
(74) *Attorney, Agent, or Firm* — Gavrilovich, Dodd & Lindsey LLP

(57) ABSTRACT

A method of generating an asymmetric closed-ended double stranded nucleic acid template from a double stranded nucleic acid template having free 5' and 3' ends by use of hairpin or dumbbell adaptors, and sequencing therefrom.

21 Claims, 9 Drawing Sheets

Specification includes a Sequence Listing.

SEQUENCE LISTING

<160> NUMBER OF SEQ ID NOS: 2

<210> SEQ ID NO 1
<211> LENGTH: 56
<212> TYPE: DNA
<213> ORGANISM: Artificial Sequence
<220> FEATURE:
<223> OTHER INFORMATION: TelN recognition sequence

<400> SEQUENCE: 1
tatcagcaca caattgccca ttatacgcgc gtataatgga ctattgtgtg ctgata      56

<210> SEQ ID NO 2
<211> LENGTH: 56
<212> TYPE: DNA
<213> ORGANISM: Artificial Sequence
<220> FEATURE:
<223> OTHER INFORMATION: TelN recognition sequence

<400> SEQUENCE: 2
atagtcgtgt gttaacgggt aatatgcgcg catattacct gataacacac gactat      56

METHODS FOR GENERATING, AND SEQUENCING FROM, ASYMMETRIC ADAPTORS ON THE ENDS OF POLYNUCLEOTIDE TEMPLATES COMPRISING HAIRPIN LOOPS

CROSS REFERENCE TO RELATED APPLICATIONS

This application is a U.S. National Phase Application filed under 35 U.S.C. § 371 and claims priority to International Application No. PCT/EP2020/079902, filed Oct. 23, 2020, which application claim priority under 35 U.S.C. § 119 (e) from U.S. Provisional Application No. 62/926,360, filed Oct. 25, 2019, the disclosures of which are incorporated herein by reference for all purposes.

FIELD OF THE INVENTION

The disclosure relates generally to methods for generating asymmetric adaptors on the ends of polynucleotides comprising hairpin loops, and sequencing therefrom.

INCORPORATION BY REFERENCE OF SEQUENCE LISTING

Accompanying this filing is a Sequence Listing entitled, "Sequence-Listing_ST25.txt" created on Oct. 19, 2020 and having 784 bytes of data, machine formatted on IBM-PC, MS-Windows operating system. The sequence listing is hereby incorporated by reference in its entirety for all purposes.

BACKGROUND

Sequencing platforms that employ closed-ended double stranded templates ideally require two different adaptor sequences at the ends of sequencing templates. Such end asymmetry enables a single sequencing primer and polymerase to bind to only one end of the close-ended templates and generate only one sequence read per template molecule. This is not currently possible with standard library preparations, where the same sequences are appended to both ends of a template, thus introducing Poisson artefacts to sequencing, i.e., some templates have no primer/polymerase bound, some have one and some have to (one at each end).

SUMMARY

The disclosure provides methods for generating asymmetric adaptors on the ends of polynucleotide templates comprising hairpin loops. By enabling asymmetric adaptors, Poisson artefacts send with standard methodologies can be avoided, thereby increasing the conversion yield of sequencing libraries. Further, the methods disclosed herein simplify library preparation workflow and allow for some steps of library preparation to be conducted on the sequencing platform.

In one embodiment, the disclosure provides a method of generating an asymmetric closed-ended double stranded nucleic acid template from a double stranded nucleic acid template having free 5' and 3' ends, comprising: (A) attaching a first nucleic acid-based hairpin or dumbbell adaptor to the 3' ends of a double stranded nucleic acid template comprising free 5' and 3' ends; (B) extending from each 3' end of the nucleic acid hairpin a sequence complementary to the double stranded nucleic acid template using a processive polymerase to generate two long hairpin duplex templates, wherein one end of the duplex template comprises a closed hairpin (the "hairpin end") and the other end of the duplex comprises a free 3'-strand end and a free 5'-strand end (the "free end"); (C) closing the free end of each long hairpin duplex template to form an asymmetric closed-ended double stranded nucleic acid template by: (i) ligating a second nucleic acid-based hairpin or dumbbell adaptor to the free end of the duplex template; or (ii) using a TelN Protelomerase to close the free end of the duplex template, wherein the free end of the duplex template is designed to include a TelN recognition sequence. In a further embodiment of an embodiment presented herein, the double stranded nucleic acid template is a double stranded DNA template. In another embodiment of an embodiment presented herein, the 5' and 3' ends of the double stranded nucleic acid template are dephosphorylated and end repaired. In yet another embodiment of an embodiment presented herein, the double stranded nucleic acid template has blunt 5' and 3' ends. In another embodiment of an embodiment presented herein, the double stranded nucleic acid template has A-tailed 3' ends. In a further embodiment of an embodiment presented herein, the first nucleic acid-based hairpin or dumbbell adaptor is ligated to the 3' ends of the double stranded nucleic acid template using a ligase. In yet a further embodiment of an embodiment presented herein, the ligase is a T4 DNA Ligase or a T3 DNA ligase. In another embodiment of an embodiment presented herein, the first nucleic acid-based hairpin or dumbbell adaptor comprises blunt ends or T-tailed ends. In yet another embodiment of an embodiment presented herein, the first nucleic acid-based hairpin adaptor is a Y-shaped adaptor. In a certain embodiment of an embodiment presented herein, dimers formed from two first nucleic acid-based hairpin or dumbbell adaptors being bound to each other are removed by using size-selection or size-exclusion techniques. In another embodiment of an embodiment presented herein, the processive polymerase is Phi29 polymerase. In yet another embodiment of an embodiment presented herein, the second nucleic acid-based hairpin or dumbbell adaptor comprises blunt ends or T-tailed ends. In a further embodiment of an embodiment presented herein, prior to step (C) the long hairpin duplex templates are digested with a restriction enzyme that creates a 5' overhang. In yet a further embodiment of an embodiment presented herein, prior to step (C) the long hairpin duplex templates are digested with a restriction enzyme that creates a 3' overhang. In another embodiment of an embodiment presented herein, the second nucleic acid-based hairpin or dumbbell adaptor comprises an overhang sequence that is complementary to the overhang sequence of the digested long hairpin duplex templates. In another embodiment of an embodiment presented herein, the second nucleic acid-based hairpin or dumbbell adaptor are ligated to the free end of the duplex template using a polynucleotide kinase and a ligase. In yet another embodiment of an embodiment presented herein, dimers formed from two second nucleic acid-based hairpin or dumbbell adaptors being bound to each other are removed by using size-selection or size-exclusion techniques. In a further embodiment of an embodiment presented herein, the TelN Protelomerase is from phage N15, and the TelN Protelomerase cuts the long hairpin duplex templates at the TelN recognition sequence and leaves covalently closed ends at the site of cleavage. In yet a further embodiment of an embodiment presented herein, a method disclosed herein further comprises the step of: (C') generating nanoball complexes comprising polycistronic amplified asymmetric closed-ended double stranded nucleic acid templates using rolling circle replication. In another embodiment of an embodiment presented herein, a method disclosed herein further comprises the step of: (D) sequencing the asymmetric closed-ended double stranded nucleic acid template or nanoball complexes using a sequencing primer and a polymerase. In yet another embodiment of an embodiment presented herein, step (B) step (C) (ii) and step (D) can be combined together as a one-pot reaction. In a further embodiment of an embodiment presented herein, step (B), step (C) (ii) and step (D) are carried out in a well of an automated sequencing platform.

In a certain embodiment, the disclosure also provides a method of generating an asymmetric double stranded nucleic acid template from tagmented DNA comprising complementary hairpin loops, comprising: (I) generating tagmented DNA comprising complementary hairpin loops at the 5' ends of each strand, wherein the hairpin loops comprise a base paired transposase recognition sequence, and wherein there is a gap of single stranded sequence between the 5' ends and the 3' ends of the tagmented DNA; (II) filing in the gaps between the 5' ends and the 3' ends of the tagmented DNA using a gap-fill-ligation reaction to form closed ended tagmented DNA; (III) generating a nick in the top strand at each hairpin region of the closed ended tagmented DNA; (IV) extending from each nick a sequence complementary to the double stranded nucleic acid template using a processive polymerase to generate two long hairpin duplex templates, wherein one end of the duplex template comprises a closed hairpin (the "hairpin end") and the other end of the duplex comprises a 3'-strand end and a 5'-strand end (the "free end"); (V) closing the free end of each long hairpin duplex template to form an asymmetric closed-ended double stranded nucleic acid template by: (a) ligating a nucleic acid-based hairpin or dumbbell adaptor to the free end of the duplex template; or (b) using a TelN Protelomerase to close the free end of the duplex template, wherein the free end of the duplex template is designed to include a TelN recognition sequence. In a further embodiment of an embodiment presented herein, the transposase recognition sequence is a 19-bp Mosaic End sequence. In yet a further embodiment of an embodiment presented herein, the gap is 9 base pairs in length. In another embodiment of an embodiment presented herein, the gap-fill-ligation reaction comprises Klenow fragment. In yet another embodiment of an embodiment presented herein, the gap-fill-ligation reaction comprises T4 DNA polymerase and Ampligase. In a certain embodiment of an embodiment presented herein, the nick is generated by using a site-specific endonuclease.

In a further embodiment of an embodiment presented herein, the processive polymerase is Phi29 polymerase. In yet a further embodiment of an embodiment presented herein, the nucleic acid-based hairpin or dumbbell adaptor comprises blunt ends or T-tailed ends. In another embodiment of an embodiment presented herein, prior to step (V) the long hairpin duplex templates are digested with a restriction enzyme that creates a 5' overhang. In yet another embodiment of an embodiment presented herein, prior to step (V) the long hairpin duplex templates are digested with a restriction enzyme that creates a 3' overhang. In a further embodiment of an embodiment presented herein, the nucleic acid-based hairpin or dumbbell adaptor comprises an overhang sequence that is complementary to the overhang sequence of the digested long hairpin duplex templates. In yet a further embodiment of an embodiment presented herein, the nucleic acid-based hairpin or dumbbell adaptor are ligated to the free end of the duplex template using a polynucleotide kinase and a ligase. In another embodiment of an embodiment presented herein, dimers formed from two nucleic acid-based hairpin or dumbbell adaptors being bound to each other are removed by using size-selection or size-exclusion techniques. In yet another embodiment of an embodiment presented herein, the TelN Protelomerase is from phage N15, and the TelN Protelomerase cuts the long hairpin duplex templates at the TelN recognition sequence and leaves covalently closed ends at the site of cleavage. In a further embodiment of an embodiment presented herein, the method further comprises the step of: (V') generating nanoball complexes comprising polycistronic amplified asymmetric closed-ended double stranded nucleic acid templates using rolling circle replication. In yet a further embodiment of an embodiment presented herein, the method further comprises the step of: (VI) sequencing the asymmetric closed-ended double stranded nucleic acid template or nanoball complexes using a sequencing primer and a polymerase. In another embodiment of an embodiment presented herein, step (V) (ii) and step (VI) can be combined together into a single step. In yet another embodiment of an embodiment presented herein, step (V) (ii) and step (VII) are carried out in a well of an automated sequencing platform.

In a particular embodiment, the disclosure also provides a method of sequencing tagmented DNA comprising complementary hairpin loops, comprising: (I) generating tagmented DNA comprising complementary hairpin loops at the 5' ends of each strand, wherein the hairpin loops comprise a base paired transposase recognition sequence, and wherein there is a gap of single stranded sequence between the 5' ends and the 3' ends of the tagmented DNA; (II) forming two extended strands of tagmented DNA comprising a transposase recognition sequence and complementary transposase recognition sequence at 5' and 3' ends of each extended strand of tagmented DNA by using a polymerase; (III) separating the extended strands of tagmented DNA and rehybridizing the transposase recognition sequences and complementary transposase recognition sequences at the ends of each of the extended strands of tagmented DNA to form to complementary hairpin loops; and (IV) sequencing the extended strand of tagmented DNA comprising complementary hairpin loops by using a sequencing polymerase. In another embodiment of an embodiment presented herein, step (IV) is carried out in a well of an automated sequencing platform. In yet another embodiment of an embodiment presented herein, prior to sequencing of step (IV): (III') generating nanoball complexes comprising polycistronic amplified extended strands of tagmented DNA.

DETAILED DESCRIPTION

Figure 1:
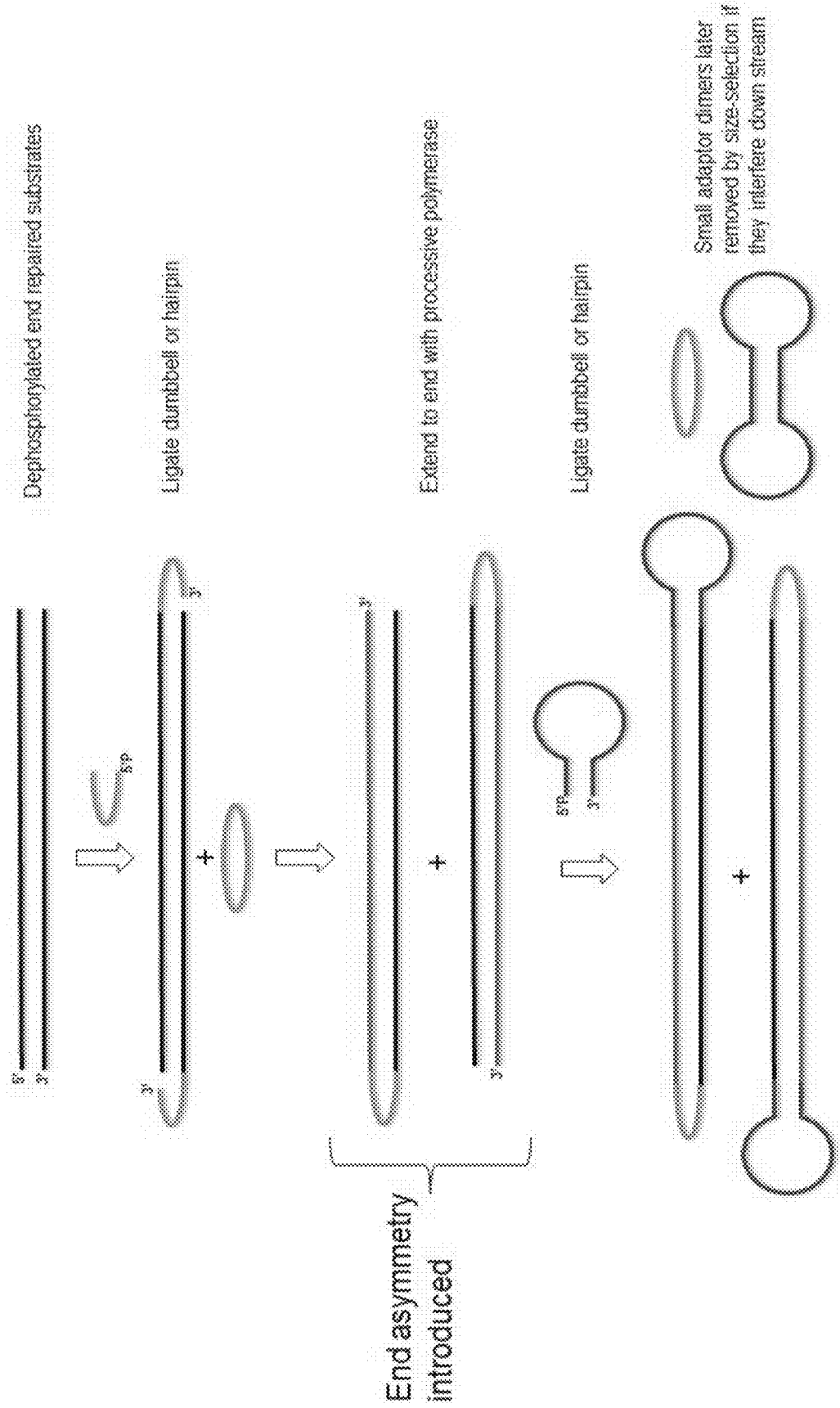
FIG. 1 provides a schematic illustrating a method for generating template end asymmetry by creating a hairpin end and a free end by ligating the 5' of a hairpin to the 3' ends of a double stranded polynucleotide template and extending the 3' end of the hairpin using a processive polymerase. An additional hairpin or dumbbell can be ligated to free end of the asymmetric template to provide a closed ended template comprising asymmetrical regions. Small adaptor dimers can be removed using size-selection or size exclusion technologies.

WM As used herein, the terms "includes," "including," "includes," "including," "contains," "containing," "have," "having," and any variations thereof, are intended to cover a non-exclusive inclusion, such that a process, method, product-by-process, or composition of matter that includes, includes, or contains an element or list of elements does not include only those elements but can include other elements not expressly listed or inherent to such process, method, product-by-process, or composition of matter. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

As used herein, the singular forms "a", "an" and "the" include plural referents unless the content clearly dictates otherwise. Thus, for example, reference to "a protein" includes a mixture of two or more proteins, and the like.

Also, the use of "or" means "and/or" unless stated otherwise.

Other than in the operating examples, or where otherwise indicated, all numbers expressing quantities of ingredients or reaction conditions used herein should be understood as modified in all instances by the term "about." The term "about" when used to described embodiments of the disclosure, in connection with percentages means ±1%, ±2%, ±3%, ±4%, ±5%. The term "about," as used herein can mean within an acceptable error range for the particular value as determined by one of ordinary skill in the art, which can depend in part on how the value is measured or determined, e.g., the limitations of the measurement system. Alternatively, "about" can mean a range of plus or minus 20%, plus or minus 10%, plus or minus 5%, or plus or minus 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value can be assumed. Also, where ranges and/or subranges of values are provided, the ranges and/or subranges can include the endpoints of the ranges and/or subranges. In some cases, variations can include an amount or concentration of 20%, 10%, 5%, 1%, 0.5%, or even 0.1% of the specified amount.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

It should be understood that this disclosure is not limited to the particular methodology, protocols, and reagents, etc., described herein and as such may vary. The terminology used herein is for the purpose of describing particular embodiments or aspects only and is not intended to limit the scope of the present disclosure.

As used herein, the term "adaptor" is a single-stranded or a double-stranded nucleic acid molecule that can be linked to the end of other nucleic acids. For purposes of this disclosure, an "adaptor" comprises a hairpin or dumbbell loop, unless stated otherwise. In a particular embodiment, an adaptor of the disclosure is a double-stranded nucleic acid (e.g., oligonucleotides) that comprises single-stranded nucleotide overhangs at the 5' and/or 3' ends. In a further embodiment, the single-stranded overhangs are 1, 2, 3, 4, 5, 6, 7, 8, 9, 10 to 20 nucleotides.

As used herein, the term "complementary" when used in reference to a polynucleotide is intended to mean a polynucleotide that includes a nucleotide sequence capable of selectively annealing to an identifying region of a target polynucleotide under certain conditions. As used herein, the term "substantially complementary" and grammatical equivalents is intended to mean a polynucleotide that includes a nucleotide sequence capable of specifically annealing to an identifying region of a target polynucleotide under certain conditions. Annealing refers to the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions can also contribute to duplex stability. Conditions under which a polynucleotide anneals to complementary or substantially complementary regions of target nucleic acids are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349 (1968). Annealing conditions will depend upon the particular application, and can be routinely determined by persons skilled in the art, without undue experimentation.

As used herein, the term "dNTP" refers to deoxynucleoside triphosphates. NTP refers to ribonucleotide triphosphates. The purine bases (Pu) include adenine (A), guanine (G) and derivatives and analogs thereof. The pyrimidine bases (Py) include cytosine (C), thymine (T), uracil (U) and derivatives and analogs thereof. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

As used herein, the term "hybridization" refers to the process in which two single-stranded polynucleotides bind non-covalently to form a stable double-stranded polynucleotide. A resulting double-stranded polynucleotide is a "hybrid" or "duplex." Hybridization conditions will typically include salt concentrations of less than about 1 M, more usually less than about 500 mM and may be less than about 200 mM. A hybridization buffer includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, i.e., conditions under which a probe will hybridize to its target subsequence but will not hybridize to the other, uncomplimentary sequences. Stringent conditions are sequence-dependent and are different in different circumstances, and may be determined routinely by those skilled in the art.

As used herein, the term "label" refers to a process in which a component, e.g., an adaptor, is modified, e.g., binding to another molecule, so that to facilitate separation of the component and its associated elements.

As used herein, the terms "ligation," "ligating," and grammatical equivalents thereof are intended to mean to form a covalent bond or linkage between the termini of two or more nucleic acids, e.g., oligonucleotides and/or polynucleotides, typically in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921, incorporated herein by reference in their entireties. The term "ligation" also encompasses non-enzymatic formation of phosphodiester bonds, as well as the formation of non-phosphodiester covalent bonds between the ends of oligonucleotides, such as phosphorothioate bonds, disulfide bonds, and the like.

As used herein, the term "nucleic acid" means single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, tetraalkylammonium, $Mg^{2+}$, $Na^+$ and the like. A nucleic acid can be a polynucleotide or an oligonucleotide. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotides analogs. Nucleic acid typically ranges in size from a few monomeric units, e.g., 5-40, to several thousands of monomeric nucleotide units. Nucleic acids include, but are not limited to, genomic DNA, cDNA, hnRNA, mRNA, rRNA, tRNA, fragmented nucleic acid, nucleic acid obtained from sub-cellular organelles such as mitochondria or chloroplasts, and nucleic acid obtained from microorganisms or DNA or RNA viruses that may be present on or in a biological sample.

As used herein, the term "nucleotide analogs" refers to synthetic analogs having modified nucleotide base portions, modified pentose portions, and/or modified phosphate portions, and, in the case of polynucleotides, modified internucleotide linkages, as generally described elsewhere (e.g., Scheit, *Nucleotide Analogs*, John Wiley, New York, 1980; Englisch, *Angew. Chem. Int. Ed. Engl.* 30:613-29, 1991; Agarwal, *Protocols for Polynucleotides and Analogs*, Humana Press, 1994; and S. Verma and F. Eckstein, Ann. Rev. Biochem. 67:99-134, 1998). Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Exemplary modified nucleotide base portions include but are not limited to 5-methylcytosine (5mC); C-5-propynyl analogs, including but not limited to, C-5 propynyl-C and C-5 propynyl-U; 2,6-diaminopurine, also known as 2-amino adenine or 2-amino-dA); hypoxanthine, pseudouridine, 2-thiopyrimidine, isocytosine (isoC), 5-methyl isoC, and isoguanine (isoG; see, e.g., U.S. Pat. No. 5,432,272). Exemplary modified pentose portions include but are not limited to, locked nucleic acid (LNA) analogs including without limitation Bz-A-LNA, S-Me-Bz-C-LNA, dmf-G-LNA, and T-LNA (see, e.g., The Glen Report, 16(2):5, 2003; Koshkin et al., *Tetrahedron* 54:3607-30, 1998), and 2'- or 3'-modifications where the 2'- or 3'-position is hydrogen, hydroxy, alkoxy (e.g., methoxy, ethoxy, allyloxy, isopropoxy, butoxy, isobutoxy and phenoxy), azido, amino, alkylamino, fluoro, chloro, or bromo. Modified internucleotide linkages include phosphate analogs, analogs having achiral and uncharged intersubunit linkages (e.g., Sterchak, E. P. et al., *Organic Chem.*, 52:4202, 1987), and uncharged morpholino-based polymers having achiral intersubunit linkages (see, e.g., U.S. Pat. No. 5,034,506). Some internucleotide linkage analogs include morpholidate, acetal, and polyamide-linked heterocycles.

In the context of "polynucleotides," the terms "variant" and "derivative" as used herein refer to a polynucleotide that comprises a nucleotide sequence of a polynucleotide or a fragment of a polynucleotide, which has been altered by the introduction of nucleotide substitutions, deletions or additions. A variant or a derivative of a polynucleotide can be a fusion polynucleotide which contains part of the nucleotide sequence of a polynucleotide. The term "variant" or "derivative" as used herein also refers to a polynucleotide or a fragment thereof, which has been chemically modified, e.g., by the covalent attachment of any type of molecule to the polynucleotide. For example, but not by way of limitation, a polynucleotide or a fragment thereof can be chemically modified, e.g., by acetylation, phosphorylation, methylation, etc. The variants or derivatives are modified in a manner that is different from naturally occurring or starting nucleotide or polynucleotide, either in the type or location of the molecules attached. Variants or derivatives further include deletion of one or more chemical groups which are naturally present on the nucleotide or polynucleotide. A variant or a derivative of a polynucleotide or a fragment of a polynucleotide can be chemically modified by chemical modifications using techniques known to those of skill in the art, including, but not limited to specific chemical cleavage, acetylation, formulation, etc. Further, a variant or a derivative of a polynucleotide or a fragment of a polynucleotide can contain one or more dNTPs or nucleotide analogs. A polynucleotide variant or derivative may possess a similar or identical function as a polynucleotide or a fragment of a polynucleotide described herein. A polynucleotide variant or derivative may possess an additional or different function compared with a polynucleotide or a fragment of a polynucleotide described herein.

As used herein, the term "tagmentation," "tagment," or "tagmenting" refers to transforming a nucleic acid, e.g., a DNA, into adaptor-modified templates in solution ready for cluster formation and sequencing by the use of transposase mediated fragmentation and tagging. This process often involves the modification of the nucleic acid by a transposome complex comprising transposase enzyme complexed with adaptors comprising transposon end sequence. Tagmentation results in the simultaneous fragmentation of the nucleic acid and ligation of the adaptors to the 5' ends of both strands of duplex fragments. Following a purification step to remove the transposase enzyme, additional sequences are added to the ends of the adapted fragments by PCR.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target nucleic acid with which it is incubated, for example, in an in vitro transposition reaction. A transposase as presented herein can also include integrases from retrotransposons and retroviruses. Transposases, transposomes and transposome complexes are generally known to those of skill in the art, as exemplified by the disclosure of US Pat. Publ. No. 2010/0120098, the content of which is incorporated herein by reference in its entirety. Although many embodiments described herein refer to Tn5 transposase and/or hyperactive Tn5 transposase, it will be appreciated that any transposition system that is capable of inserting a transposon end with sufficient efficiency to 5'-tag and fragment a target nucleic acid for its intended purpose can be used in the present invention. In particular embodiments, a preferred transposition system is capable of inserting the transposon end in a random or in an almost random manner to 5'-tag and fragment the target nucleic acid.

As used herein, the term "transposition reaction" refers to a reaction wherein one or more transposons are inserted into target nucleic acids, e.g., at random sites or almost random sites. Essential components in a transposition reaction are a transposase and DNA oligonucleotides that exhibit the nucleotide sequences of a transposon, including the transferred transposon sequence and its complement (the non-transferred transposon end sequence) as well as other components needed to form a functional transposition or transposome complex. The DNA oligonucleotides can further comprise additional sequences (e.g., adaptor or primer sequences) as needed or desired. In some embodiments, the method provided herein is exemplified by employing a transposition complex formed by a hyperactive Tn5 transposase and a Tn5-type transposon end (Goryshin and Reznikoff, 1998, *J. Biol. Chem.*, 273: 7367) or by a MuA transposase and a Mu transposon end comprising R1 and R2 end sequences (Mizuuchi, 1983, *Cell*, 35: 785; Savilahti et al., 1995, *EMBO J.*, 14: 4893). However, any transposition system that is capable of inserting a transposon end in a random or in an almost random manner with sufficient efficiency to 5'-tag and fragment a target DNA for its intended purpose can be used in the present invention. Examples of transposition systems known in the art which can be used for the present methods include but are not limited to *Staphylococcus aureus* Tn552 (Colegio et al., 2001, *J Bacteriol.*, 183: 2384-8; Kirby et al., 2002, *Mol Microbiol*, 43: 173-86), Ty1 (Devine and Boeke, 1994, *Nucleic Acids Res.*, 22: 3765-72 and International Patent Application No. WO 95/23875), Transposon Tn7 (Craig, 1996, *Science.* 271: 1512; Craig, 1996, Review in: *Curr Top Microbiol Immunol*, 204: 27-48), Tn10 and IS10 (Kleckner et al., 1996, *Curr Top Microbiol Immunol*, 204: 49-82), Mariner transposase (Lampe et al., 1996, *EMBO J.*, 15: 5470-9), Tci (Plasterk, 1996, *Curr Top Microbiol Immunol*, 204: 125-43), P Element (Gloor, 2004, *Methods Mol Biol*, 260: 97-114), TnJ (Ichikawa and Ohtsubo, 1990, *J Biol Chem.* 265: 18829-32), bacterial insertion sequences (Ohtsubo and Sekine, 1996, *Curr. Top. Microbiol. Immunol.* 204:1-26), retroviruses (Brown et al., 1989, *Proc Natl Acad Sci USA*, 86: 2525-9), and retrotransposon of yeast (Boeke and Corces, 1989, *Annu Rev Microbiol.* 43: 403-34). The method for inserting a transposon end into a target sequence can be carried out in vitro using any suitable transposon system for which a suitable in vitro transposition system is available or that can be developed based on knowledge in the art. In general, a suitable in vitro transposition system for use in the methods provided herein requires, at a minimum, a transposase enzyme of sufficient purity, sufficient concentration, and sufficient in vitro transposition activity and a transposon end with which the transposase forms a functional complex with the respective transposase that is capable of catalyzing the transposition reaction. Suitable transposase transposon end sequences that can be used in the invention include but are not limited to wild-type, derivative or mutant transposon end sequences that form a complex with a transposase chosen from among a wild-type, derivative or mutant form of the transposase.

As used herein, the term "transposome complex" refers to a transposase enzyme non-covalently bound to a double stranded nucleic acid. For example, the complex can be a transposase enzyme preincubated with double-stranded transposon DNA under conditions that support non-covalent complex formation. Double-stranded transposon DNA can include, without limitation, Tn5 DNA, a portion of Tn5 DNA, a transposon end composition, a mixture of transposon end compositions or other double-stranded DNAs capable of interacting with a transposase such as the hyperactive Tn5 transposase.

The term "transposon end" (TE) refers to a double-stranded nucleic acid, e.g., a double-stranded DNA that exhibits only the nucleotide sequences (the "transposon end sequences") that are necessary to form the complex with the transposase or integrase enzyme that is functional in an in vitro transposition reaction. In some embodiments, a transposon end is capable of forming a functional complex with the transposase in a transposition reaction. As non-limiting examples, transposon ends can include the 19-bp outer end ("OE") transposon end, inner end ("IE") transposon end, or "mosaic end" ("ME") transposon end recognized by a wild-type or mutant Tn5 transposase, or the R1 and R2 transposon end as set forth in the disclosure of US Pat. Publ. No. 2010/0120098, the content of which is incorporated herein by reference in its entirety. Transposon ends can include any nucleic acid or nucleic acid analogue suitable for forming a functional complex with the transposase or integrase enzyme in an in vitro transposition reaction. For example, the transposon end can include DNA, RNA, modified bases, non-natural bases, modified backbone, and can include nicks in one or both strands. Although the term "DNA" is sometimes used in the present disclosure in connection with the composition of transposon ends, it should be understood that any suitable nucleic acid or nucleic acid analogue can be utilized in a transposon end.

Sequencing platforms that employ closed-ended double stranded sequencing templates typically require two different adaptor sequences at the ends of the sequencing templates. Such end asymmetry enables a single sequencing polymer and polymerase to bind to only one end of the close-ended sequencing template, and generate only one sequence read per template molecule. However, such end asymmetry is not currently employed by such sequencing platforms for library preparations. Instead, these sequencing platforms have symmetrical ends where the sequencing primer can bind at either end of the sequencing template, thus introducing Poisson artefacts to sequencing. In other words, some of the sequencing template will have no primer/polymerase bound, some sequencing templates will have one primer bound, and some sequencing templates will have two primers bound at either end of the sequencing template. With use of closed-ended sequencing templates that have asymmetric ends, these Poisson artefacts can be avoided. Accordingly, the methods of the disclosure provide a notable improvement over the state of the art by providing for the generation of closed-ended double stranded templates that have asymmetric ends by significantly increasing the conversion yield for sequencing libraries. Further, the methods of the disclosure provide for steps that can be performed in situ in the wells of a sequencing platform, allowing for library preparation to be conducted on the sequencing platform.

As shown in FIG. 1, a nucleic acid-based hairpin or dumbbell adaptor is attached to a double stranded nucleic acid template that has free 5' and 3' ends. The double stranded nucleic acid template may be dsDNA, dsRNA, or a chimeric mixture of DNA and RNA that form a double stranded molecule. The nucleotides of the nucleic acid may be comprised of naturally occurring nucleotides, e.g., A, G, C, T, and U, that are joined together via phosphodiester bond linkages. Alternatively, one or more nucleotides of the nucleic acid may be modified in some manner (e.g., a nucleotide analog). Examples of nucleotide analogs, include nucleotides or ribonucleotides which have been modified at the 2' position of ribose or deoxyribose to comprise a -methoxy-ethyl group; a —O-methyl group; a fluoro group; 2-aminopurine; 5-bromo du; deoxyUridine; 2,6-Diaminopurine; deoxyInosine; hydroxymethyl dC; 5-methyl dC; 5-Nitroindole; 5-hydroxybutynl-2'-deoxyuridine; and 8-aza-7-deazaguanosine. Further, the nucleotides may be linked together by phosphorothioate linkages in addition to phosphodiester linkages. The free 5' and 3' ends of the double stranded nucleic acid template may be blunt, or have overhang of one or more unmatched bases (e.g., a 3' overhang or a 5' overhang). In a certain embodiment, the free 5' and/or 3' ends of the double stranded nucleic acid template comprises a 3' overhang of one or more adenine bases. In a further embodiment, the 5' and/or 3' ends of the double stranded nucleic acid template have been dephosphorylated and end repaired.

Figure 2:
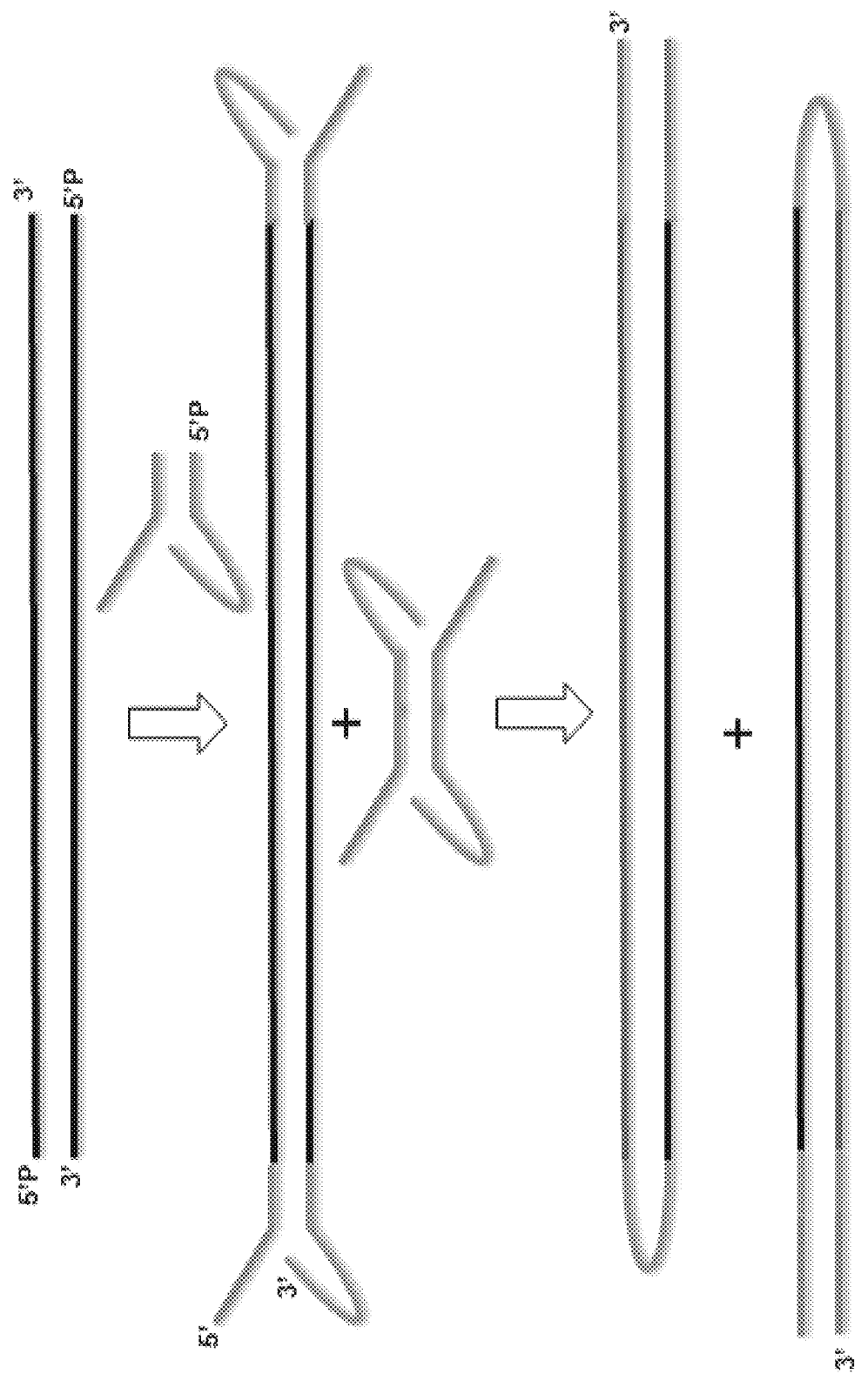
FIG. 2 provides a schematic illustrating a method for generating template end asymmetry by creating a hairpin end and a free end by ligating the 5' of a Y adaptor to the 3' ends of a double stranded polynucleotide template and extending the 3' end of the Y adaptor using a processive polymerase.

The nucleic acid-base hairpin or dumbbell adaptor comprises a sequence that loops back on itself so that the ends can be attached to a double stranded nucleic acid template. The nucleic acid-based hairpin or dumbbell adaptor can have any sequence, or can be designed to comprise a target sequence. Examples of target sequences include, but not limited to, common primer sequence(s), universal sequencing primer sequence(s), bar code sequence(s), restriction enzyme sequence(s), TelN recognition sequence(s), or any combination of the foregoing. The nucleic acid-based hairpin or dumbbell adaptor may be attached to the double stranded nucleic acid template by use of a ligase. Examples of ligases, include but are not limited to, DNA ligases, like T4 DNA ligase, *E. Coli* DNA ligase, Ampligase DNA Ligase, T3 DNA ligase, T7 DNA ligase, and Taq DNA Ligase; and RNA ligases, like T4 RNA Ligase 1, T4 RNA Ligase 2, RtcB Ligase, and *M. thermoautotrophicum* Ligase. Phosphorylation or dephosphorylation steps may be performed prior to attaching the nucleic acid-based hairpin or dumbbell adaptor to the double stranded nucleic acid template or tagmented DNA, when necessary. For purposes of this disclosure, any of the foregoing enzymes may be further modified by genetic engineering techniques in order to increase one or more functionalities of the enzyme, like processivity, thermostability, fidelity, etc. The nucleic acid-based hairpin or dumbbell adaptor may further comprise a label, so as to allow for detection and/or purification of adaptor containing sequences, such as adaptors attached to nucleic acid templates. The nucleic acid-base hairpin or dumbbell adaptor comprises a sequence that loops back on itself so that the ends can be attached to the double stranded template sequence or tagmented DNA. For the purposes of this disclosure a nucleic acid-base hairpin or dumbbell adaptor can be a Y-shaped adaptor that comprises a portion of its sequence that forms a hairpin loop. As shown in FIG. 2, Y-shaped adaptors can be used to generate an asymmetric closed-ended double stranded nucleic acid template from a double stranded nucleic acid template having free 5' and 3' ends. Moreover, any dimers formed by ligating two nucleic acid-base hairpin or dumbbell adaptors together can be removed using size-selection or size-exclusion technologies, if such dimers are inferring with downstream reactions.

The disclosure further provides for extending from each 3' end of the nucleic acid hairpin a sequence complementary to the double stranded nucleic acid template or tagmented DNA using a processive polymerase and free nucleotides (e.g., dNTPs or NTPs) to generate two long hairpin duplex templates, wherein one end of the duplex template comprises a closed hairpin (the "hairpin end") and the other end of the duplex comprises a free 3'-strand end and a free 5'-strand end (the "free end"). Examples of processive polymerases include, but are not limited to, Phi29 polymerase, SP6 RNA Polymerase, and T7 RNA Polymerase.

Figure 3:
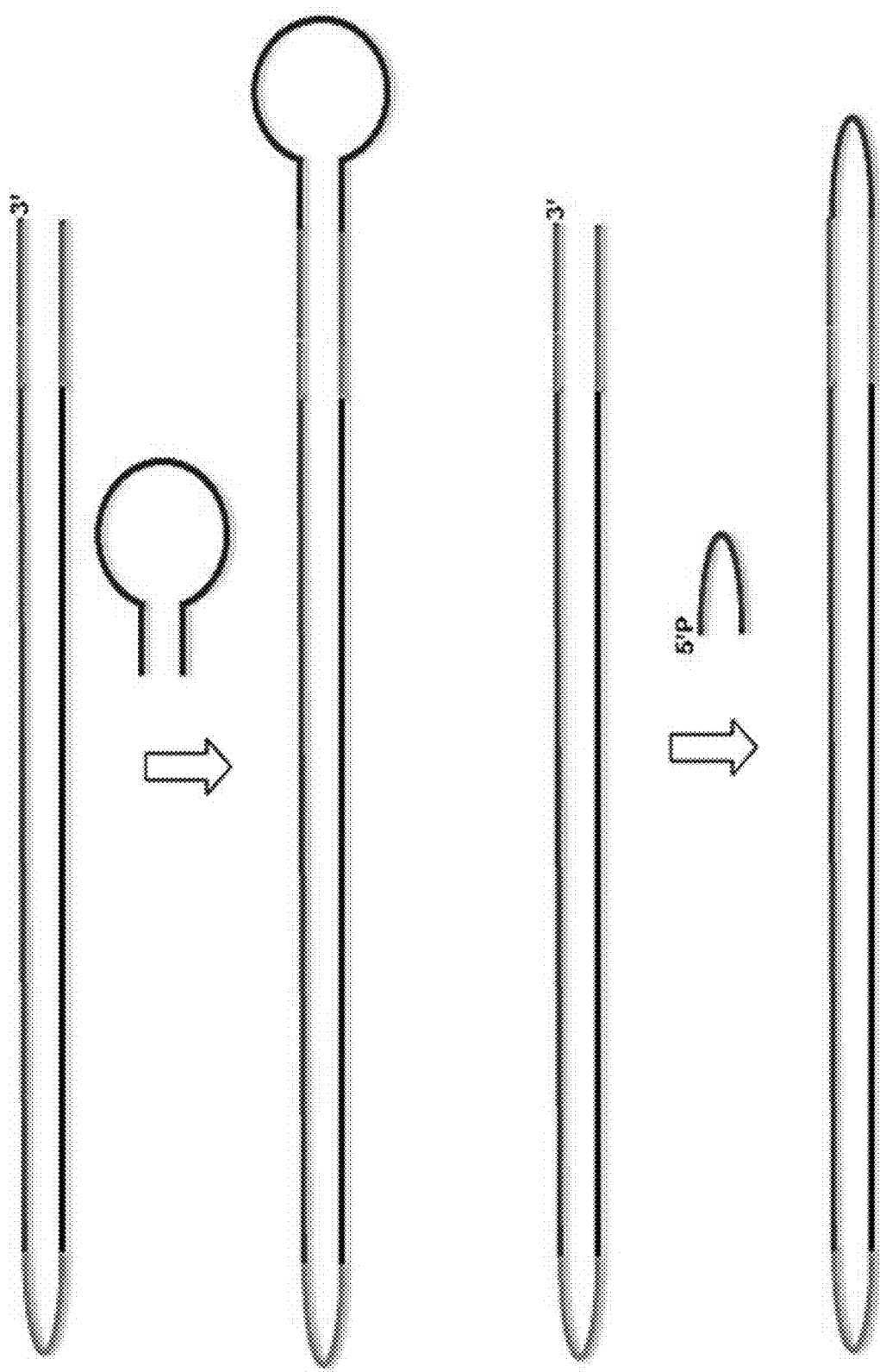
FIG. 3 provides a schematic illustrating blunt end ligation of a dumbbell adaptor or a simple hairpin adaptor to the 'free end' of asymmetric template.
Figure 4:
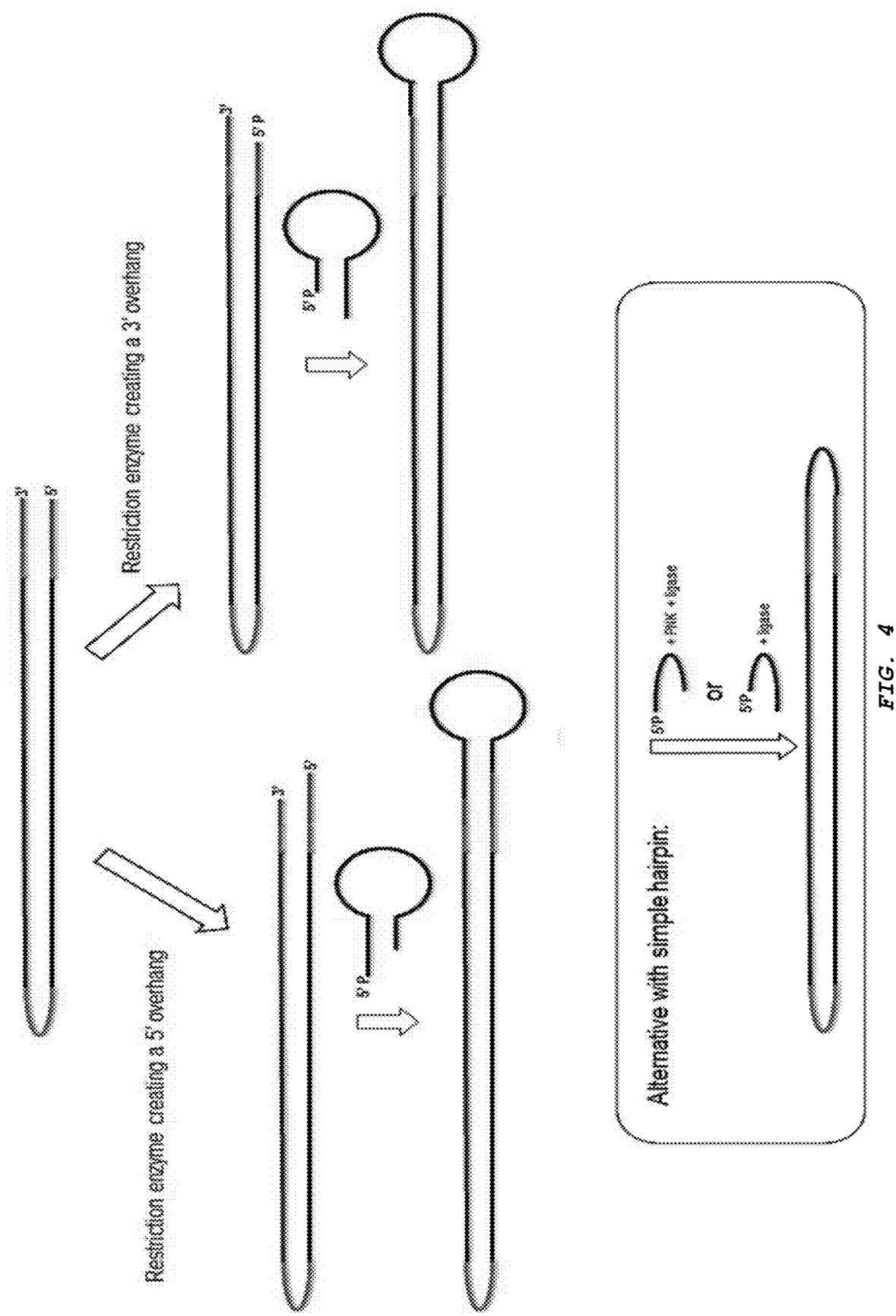
FIG. 4 provides a schematic illustrating blunt end ligation of a dumbbell adaptor or a simple hairpin adaptor having a complementary overhang sequence to a restriction digested asymmetric template having a 5' or a 3' overhang.

As shown in FIGS. 3 and 4, the disclosure also provides for closing the "free end" of the long hairpin duplex templates to form an asymmetric closed-ended double stranded nucleic acid template by attaching a second nucleic acid-based hairpin or dumbbell adaptor to the duplex template. The second nucleic acid-base hairpin or dumbbell adaptor comprises a sequence that loops back on itself so that the ends can be attached to a duplex template. As shown in FIG. 3, the second nucleic acid-based hairpin or dumbbell adaptor to the duplex template can have blunt ends and can be attached to a duplex template also having blunt ends. As shown in FIG. 4, the second nucleic acid-based hairpin or dumbbell adaptor may have 5' overhang or 3' overhang ends and be attached to a duplex template having complementary overhang ends. The overhang ends on the duplex template can be generated by digesting with a restriction enzyme, and designing the second nucleic acid-based hairpin or dumbbell adaptor to have complementary overhang ends. The second nucleic acid-based hairpin or dumbbell adaptor can have any sequence, or can be designed to comprise a target sequence. Examples of target sequences include, but not limited to, common primer sequence(s), universal sequencing primer sequence(s), bar code sequence(s), restriction enzyme sequence(s), TelN recognition sequence(s), or any combination of the foregoing. The second nucleic acid-based hairpin or dumbbell adaptor attached to the template may comprise a sequence that is less than 50%, greater than 50%, greater than 70%, greater than 80%, greater than 90%, greater than 95%, greater than 98%, or 100% identical to the nucleic acid-based hairpin or dumbbell adaptor attached to double stranded nucleic acid template or tagmented DNA. The second nucleic acid-based hairpin or dumbbell adaptor may be attached to the duplex template by use of a ligase. Examples of ligases, include but are not limited to, DNA ligases, like T4 DNA ligase, E. Coli DNA ligase, Ampligase DNA Ligase, T3 DNA ligase, T7 DNA ligase, and Taq DNA Ligase; and RNA ligases, like T4 RNA Ligase 1, T4 RNA Ligase 2, RtcB Ligase, and *M. thermoautotrophicum* Ligase. Phosphorylation or dephosphorylation steps may be performed prior to attaching the nucleic acid-based hairpin or dumbbell adaptor to the duplex template, when necessary. For purposes of this disclosure, any of the foregoing enzymes may be further modified by genetic engineering techniques in order to increase one or more functionalities of the enzyme, like processivity, thermostability, fidelity, etc. The second nucleic acid-based hairpin or dumbbell adaptor may further comprise a label, so as to allow for detection and/or purification of adaptor containing sequences, such as adaptors attached to the duplex template. Any dimers formed by ligating two second nucleic acid-base hairpin or dumbbell adaptors together can be removed using size-selection or size-exclusion technologies, if such dimers are inferring with downstream reactions. The resulting asymmetric closed-ended double stranded nucleic acid template can then be amplified by rolling circle amplification to form nanoballs. The nanoballs are loaded into wells of an automated sequencing platform; and sequencing is performed therefrom. Nanoball structures may be of sufficient size to exclude all but one template nanoball from entering a sequence well, thus avoiding multiple interfering sequencing reactions from individual wells. Moreover, nanoball workflow steps may be prepared in solution, or in tubes.

Figure 5:
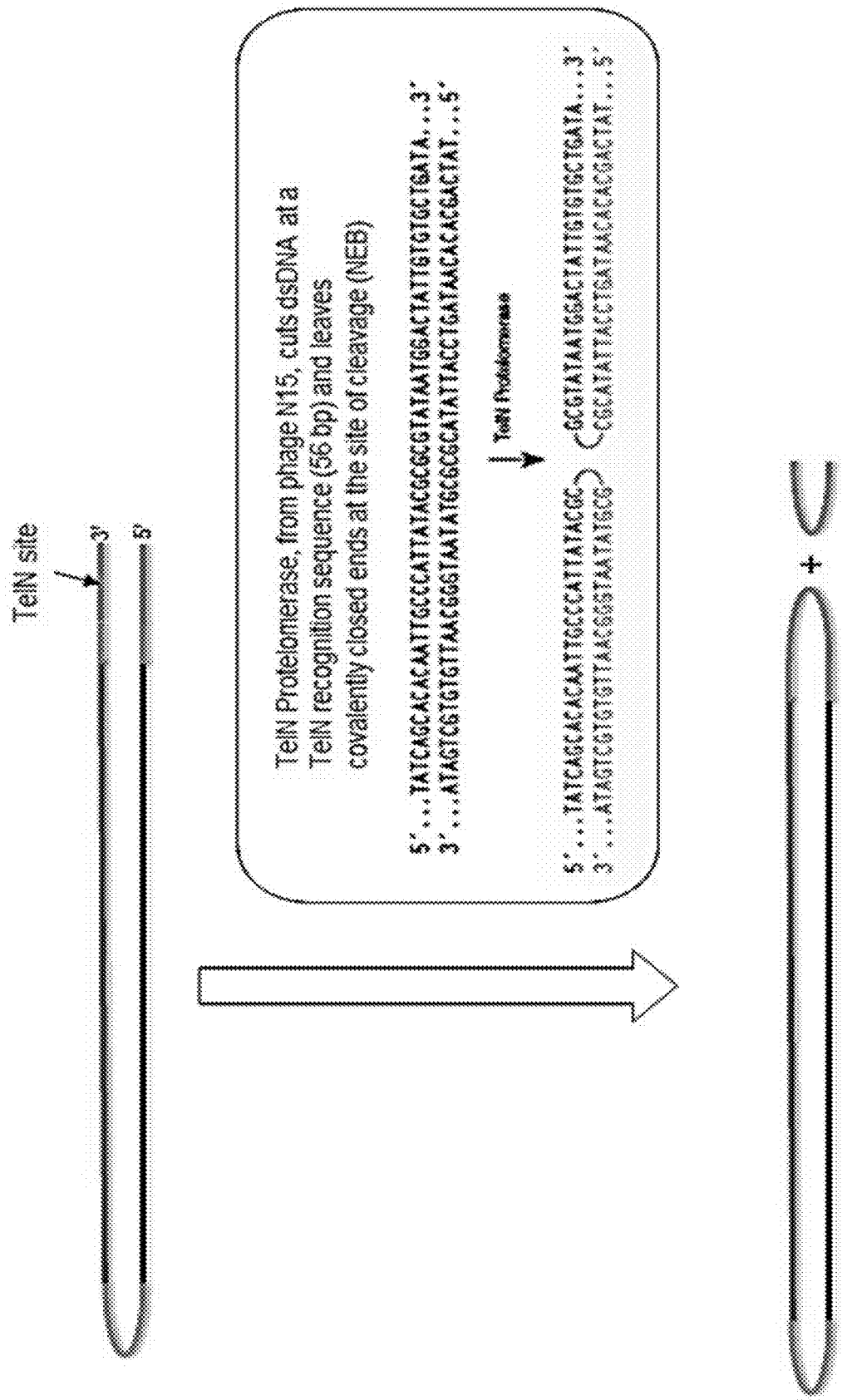
FIG. 5 provides a schematic illustrating showing inclusion of a TelN Protelomerase site in the asymmetric template sequence followed by circularization (SEQ ID NO:1 and 2).

An alternate embodiment for closing the duplex template is shown in FIG. 5. Duplex templates comprising a TelN recognition sequence, the duplex templates may be "closed" by using a TelN protelomerase (e.g., phage N15 protelomerase). In a particular embodiment, the TelN recognition sequence comprises a 56 bp sequence of:

(SEQ ID NO: 1)
5'-TATCAGCACACAATTGCCCATTATACGCGCGTATAATGGACTATTGTG

TGCTGATA-3'

(SEQ ID NO: 2)
5'-ATAGTCGTGTGTTAACGGGTAATATGCGCGCATATTACCTGATAACAC

ACGACTAT-3'

Figure 6:
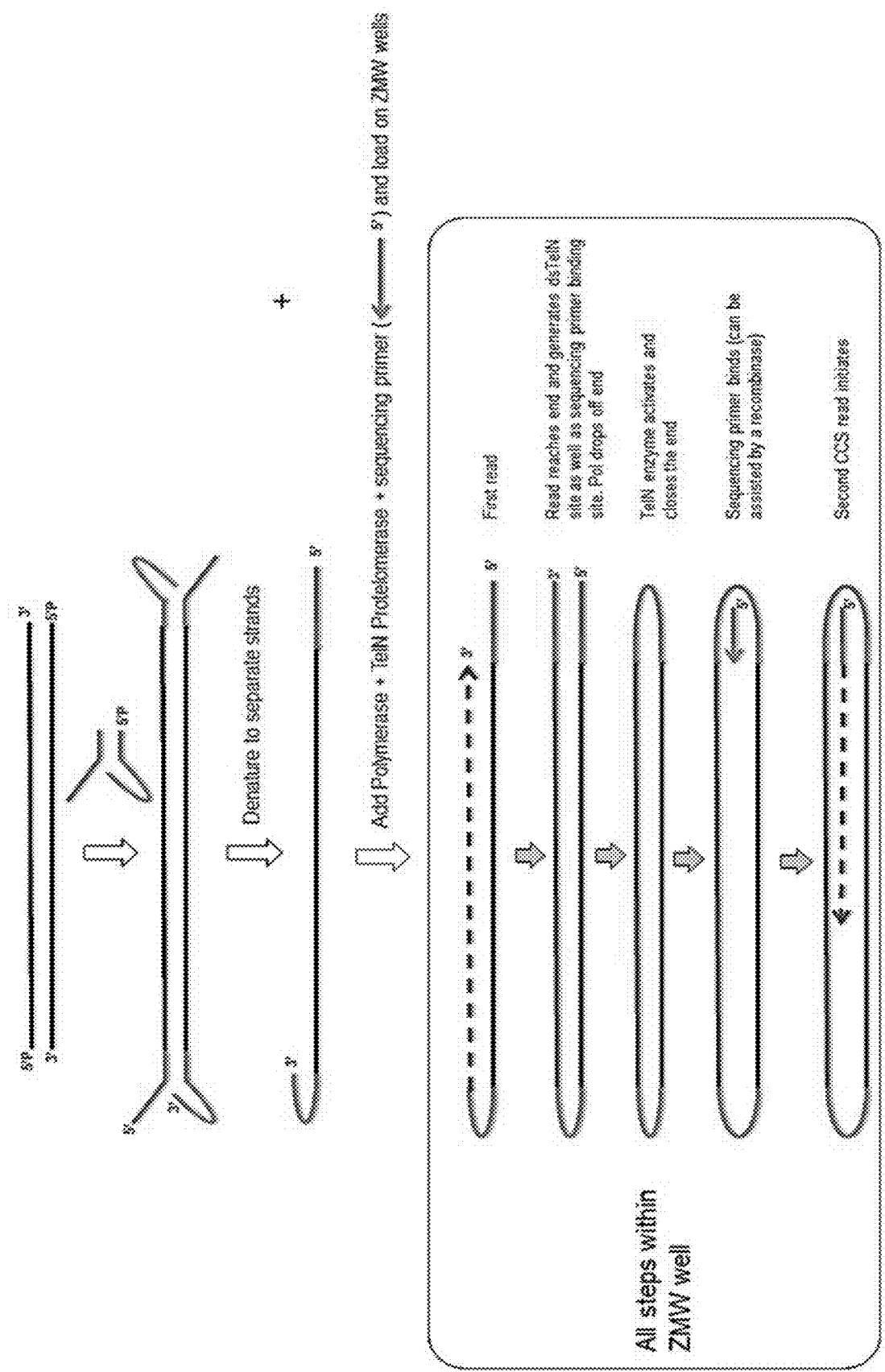
FIG. 6 provides a schematic illustrating a method where a closed ended template comprising asymmetric regions can be sequenced using an automated sequencing platform, whereby at least some of the steps, as indicated, can be performed in situ in a cell of the sequencing platform.

As shown in FIG. 6, many of the steps of the methods disclosed herein can be performed within the well of a sequence platform, like a zero-mode waveguide (ZMW) well. For example, a ZMW well can be loaded with the double stranded nucleic acid template comprising the attached hairpin or dumbbell adaptor, a polymerase, TelN Protelomerase, one or more sequencing primer(s), and reaction buffers containing dNTPS or NTPS. In the first read, the 3' end of the nucleic acid hairpin or dumbbell sequence is extended generating a duplex template comprising a closed hairpin (the "hairpin end") and the other end of the duplex comprises a free 3'-strand end and a free 5'-strand end (the "free end"). In doing so, a TelN recognition sequence is generated which is acted on by the TelN enzyme, thereby forming a closed-ended double stranded nucleic acid template that is bound by the sequencing primer and sequencing is then carried out in the automated platform in subsequent reads.

Figure 7:
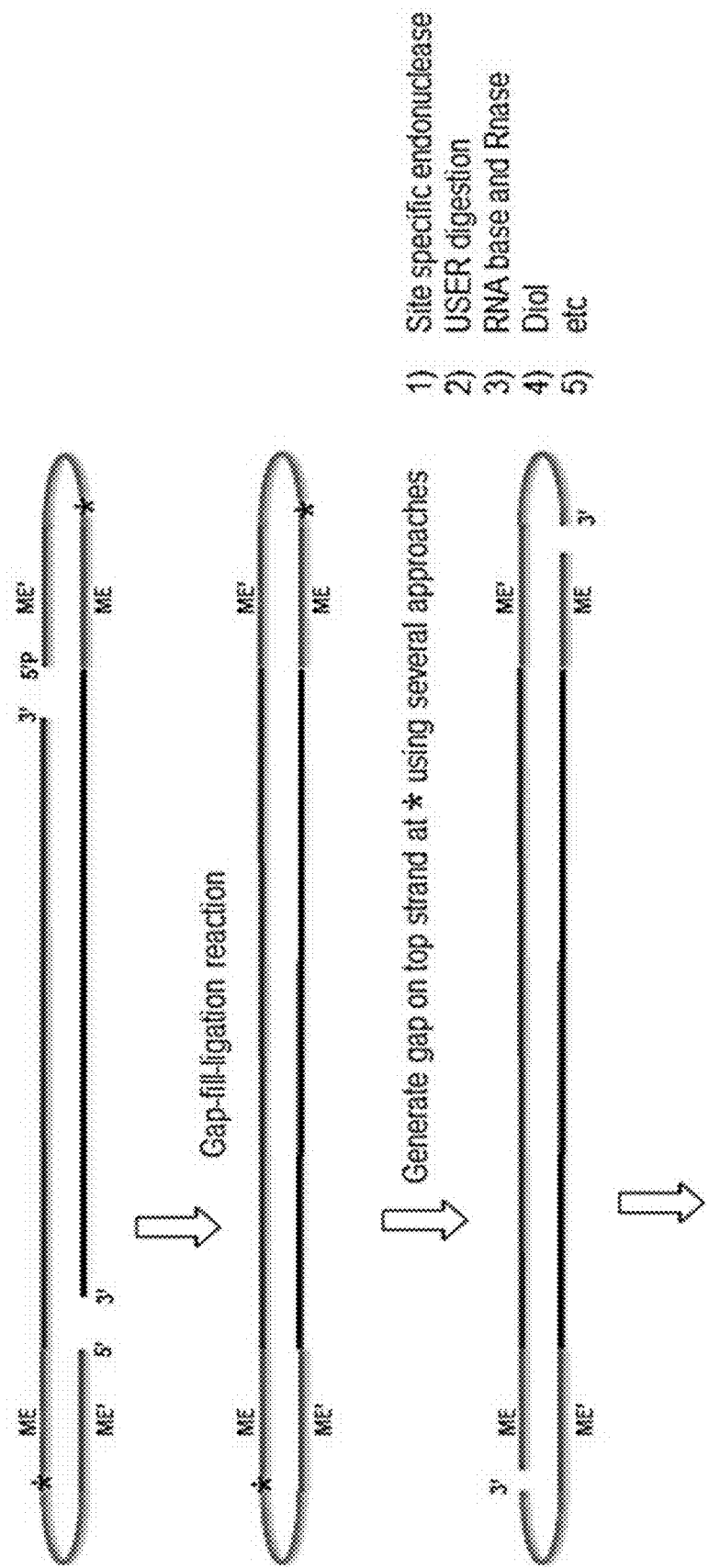
FIG. 7 provides a schematic illustrating a method for making and asymmetric ends from tagmented DNA by using a gap filing reaction and generating a nick in the top strand. Nicks in the top strand can be generated by using several approaches, including use of site-specific endonucleases, USER digestion, RNA base and Rnase, Diol, etc.
Figure 8:
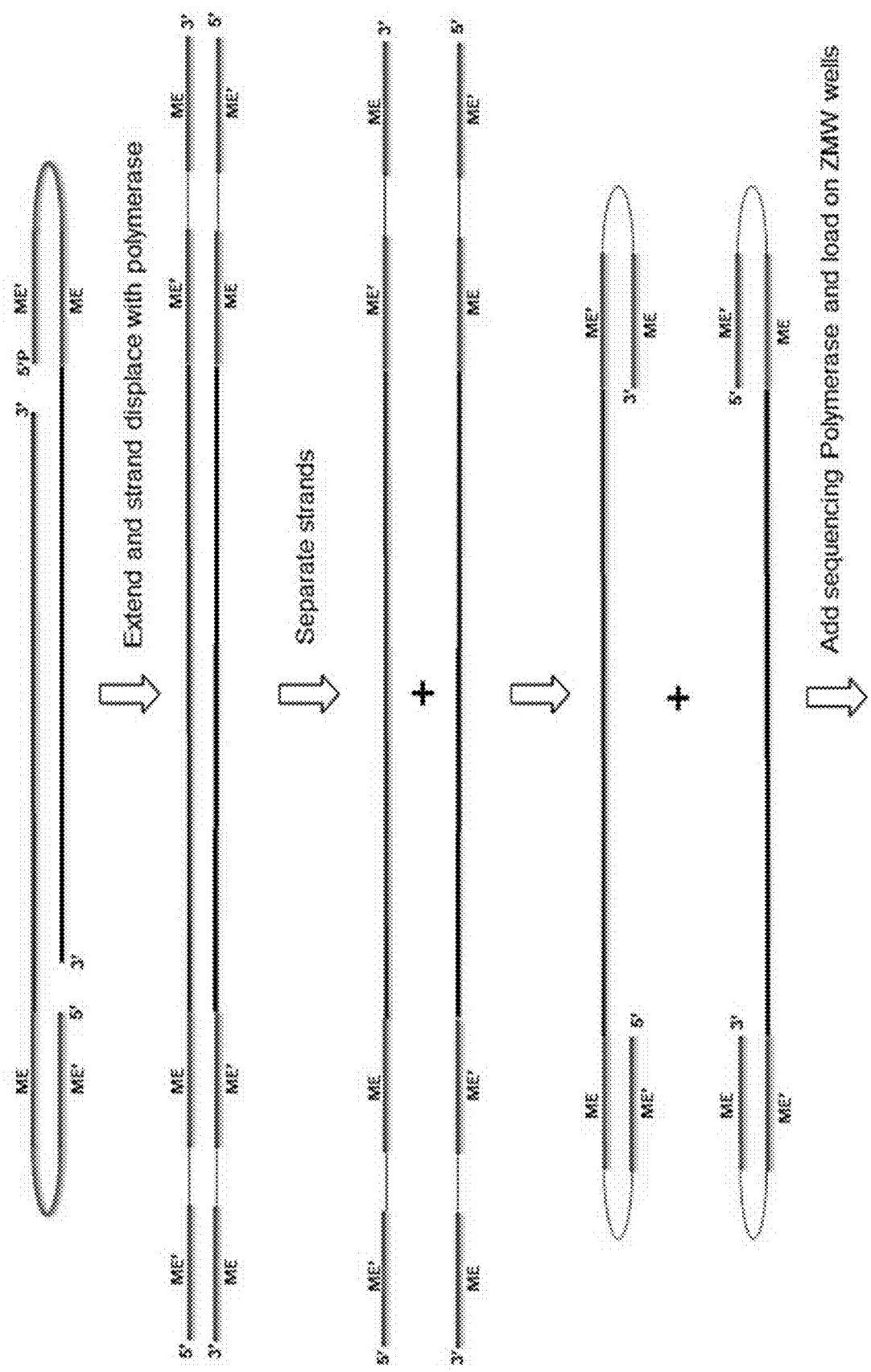
FIG. 8 provides a schematic illustrating using polymerase flush based method to generate 3' ended hairpin loops from tagmented DNA.
Figure 9:
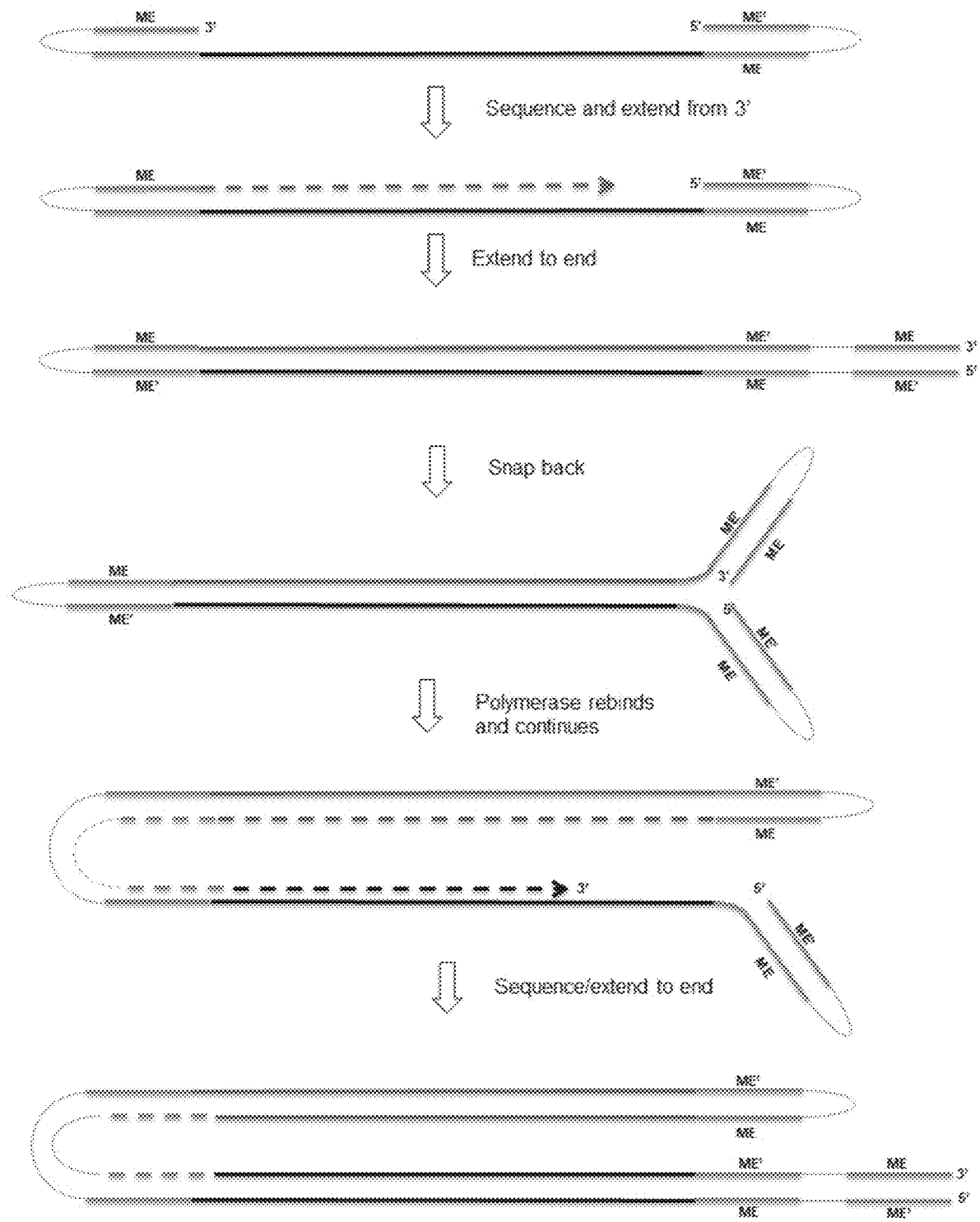
FIG. 9 provides a schematic illustrating a method for on instrument template generation and sequencing from tagmented DNA.

As shown in FIGS. 7-9, the nucleic acid-based hairpin or dumbbell adaptor is attached to a double stranded nucleic acid template via transposase mediated tagmentation or transposition reaction. Examples of such reactions are described in U.S. Publication No. 2010/0120098, which is incorporated by reference herein in its entirety. Transposomes have free DNA ends and insert randomly into DNA in a 'cut and paste' reaction. Because the DNA ends are free, this effectively fragments the DNA while adding on the nucleic acid-based hairpin or dumbbell adaptors. Exemplary transposition complexes, suitable for use in the methods provided herein, include, but are not limited to, those formed by a hyperactive Tn5 transposase and a Tn5-type transposon end or by a MuA transposase and a Mu transposon end comprising R1 and R2 end sequences, a transposase Tn3, and a Sleeping Beauty transposase (see, e.g., Goryshin and Reznikoff, *J. Biol. Chem.* 273: 7367, 1998; and Mizuuchi, *Cell* 35: 785, 1983; Savilahti et al., *EMBO J.* 14: 4893, 1995; which are incorporated by reference herein in their entireties). However, any transposition system that is capable of inserting a transposon end with sufficient efficiency to attach nucleic acid-based hairpin or dumbbell adaptors to the 5' ends of the double stranded nucleic acid template. Other examples of known transposition systems that could be used in the provided methods include, but are not limited to, *Staphylococcus aureus* Tn552, Ty1, Transposon Tn7, Tn/O and IS10, Mariner transposase, Tel, P Element, Tn3, bacterial insertion sequences, retroviruses, and retrotransposon of yeast (see, e.g., Colegio et al., 2001, *J. Bacteriol.* 183: 2384-8; kirby et al., 2002, *Mol. Microbiol.* 43: 173-86; Devine and Boeke, 1994, *Nucleic Acids Res.*, 22: 3765-72; International Patent Application No. WO 95/23875; Craig, 1996, *Science* 271:1512; Craig, 1996, Review in: *Curr Top Microbiol Immunol.* 204: 27-48; Kleckner et al., 1996, *Curr Top Microbiol Immunol.* 204: 49-82; Lampe et al., 1996, *EMBO J.* 15: 5470-9; Plasterk, 1996, *Curr Top Microbiol Immunol* 204: 125-43; Gloor, 2004, *Methods Mol. Biol.* 260: 97-114; Ichikawa and Ohtsubo, 1990, *J Biol. Chem.* 265: 18829-32; Ohtsubo and Sekine, 1996, *Curr. Top. Microbiol. Immunol.* 204: 1-26; Brown et al., 1989, *Proc Natl Acad Sci USA* 86: 2525-9; Boeke and Corces, 1989, *Annu Rev Microbiol.* 43: 403-34; which are incorporated herein by reference in their entireties). In a particular embodiment, the tagmented template comprises a mosaic end (ME) sequence, and the transposase is a Tn5 transposase.

After the transposase reaction, the resulting tagmented DNA comprising complementary hairpin loops at the 5' ends of each strand comprise single-stranded gaps (e.g., a 9 bp gap) which may be filled by using gap filling reaction using Klenow fragment, T4 DNA polymerase, and/or Ampligase (see FIG. 7). The resulting closed end tagmented DNA is then nicked in the top strand using any number of techniques, including use of site-specific endonucleases, USER digestion, incorporating an RNA base and then Rnase, Diol, etc. In particular embodiment, a site-specific endonuclease is used to create a nick in the top strand. The nicked tagmented template can be extended from each nick, a sequence complementary to the double stranded nucleic acid template, using a processive polymerase to generate two long hairpin duplex templates, wherein one end of the duplex template comprises a closed hairpin (the "hairpin end") and the other end of the duplex comprises a 3'-strand end and a 5'-strand end (the "free end"). The duplex template can be 'closed' using the same methods described above, including the use of a TelN protelomerase if the duplex template is designed to include a TelN recognition sequence.

Alternatively, a polymerase flush can be used after the transposase reaction (see FIG. 8). Tagmented DNA comprising complementary hairpin loops at the 5' ends of each strand are first generated. After which, two extended strands of tagmented DNA comprising a transposase recognition sequence and complementary transposase recognition sequence at 5' and 3' ends of each extended strand of tagmented DNA are synthesized using a polymerase. The extended strands are then separated and the transposase recognition sequences and complementary transposase recognition sequences at the ends of the tagmented DNA are reformed into hairpin loops. The extended strands comprising hairpin loops can then be loaded into a well of an automated sequencing platform and sequenced using a sequencing polymerase (see FIG. 9).

In some embodiments, the sequencing of an asymmetric closed-ended double stranded nucleic acid template includes use of one or more of sequencing by synthesis, bridge PCR, chain termination sequencing, sequencing by hybridization, nanopore sequencing, and sequencing by ligation.

In some embodiments, the sequencing methodology used in the method provided herein is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence-based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US Pat. Publ. No 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US Pat. Publ. No. 2009/0026082 A1; US Pat. Publ. No. 2009/0127589 A1; US Pat. Publ. No. 2010/0137143 A1; or US Pat. Publ. No. 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another useful sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008), the disclosures of which are incorporated herein by reference).

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of generating an asymmetric double stranded nucleic acid template from tagmented DNA comprising complementary hairpin loops, comprising:
   (I) generating tagmented DNA comprising complementary hairpin loops at the 5' ends of each strand, wherein the hairpin loops comprise a base paired transposase recognition sequence, and wherein there is a gap of single stranded sequence between the 5' ends and the 3' ends of the tagmented DNA;
   (II) filing in the gaps between the 5' ends and the 3' ends of the tagmented DNA using a gap-fill-ligation reaction to form closed ended tagmented DNA;
   (III) generating a nick in the top strand at each hairpin region of the closed ended tagmented DNA;
   (IV) extending from each nick a sequence complementary to the double stranded nucleic acid template using a processive polymerase to generate two long hairpin duplex templates, wherein one end of the duplex template comprises a closed hairpin (the "hairpin end") and the other end of the duplex template comprises a 3'-strand end and a 5'-strand end (the "free end"); and
   (V) closing the free end of each long hairpin duplex template to form an asymmetric closed-ended double stranded nucleic acid template by:
      (a) ligating a nucleic acid-based hairpin or dumbbell adaptor to the free end of the duplex template; or
      (b) using a TelN Protelomerase to close the free end of the duplex template, wherein the free end of the duplex template is designed to include a TelN recognition sequence.

2. The method of claim 1, wherein the transposase recognition sequence is a 19-bp Mosaic End sequence.

3. The method of claim 2, wherein the gap is 9 base pairs in length.

4. The method of claim 1, wherein the gap-fill-ligation reaction comprises a Klenow fragment.

5. The method of claim 1, wherein the gap-fill-ligation reaction comprises a T4 DNA polymerase and a thermostable DNA ligase.

6. The method of claim 1, wherein the nick is generated by using a site-specific endonuclease.

7. The method of claim 1, wherein the processive polymerase is Phi29 polymerase.

8. The method of claim 1, wherein the nucleic acid-based hairpin or dumbbell adaptor comprises blunt ends or T-tailed ends.

9. The method of claim 1, wherein prior to step (V) the long hairpin duplex templates are digested with a restriction enzyme that creates a 5' overhang.

10. The method of claim 9, wherein the nucleic acid-based hairpin or dumbbell adaptor comprises an overhang sequence that is complementary to the overhang sequence of the digested long hairpin duplex templates.

11. The method of claim 1, wherein prior to step (V) the long hairpin duplex templates are digested with a restriction enzyme that creates a 3' overhang.

12. The method of claim 1, wherein the nucleic acid-based hairpin or dumbbell adaptor are ligated to the free end of the duplex template using a polynucleotide kinase and a ligase.

13. The method of claim 1, wherein dimers formed from two nucleic acid-based hairpin or dumbbell adaptors being bound to each other are removed by using size-selection or size-exclusion techniques.

14. The method of claim 1, wherein the TelN Protelomerase is from phage N15, and the TelN Protelomerase cuts the long hairpin duplex templates at the TelN recognition sequence and leaves covalently closed ends at the site of cleavage.

15. The method of claim 1, wherein the method further comprises the step of:
   (V') generating nanoball complexes comprising polycistronic amplified asymmetric closed-ended double stranded nucleic acid templates using rolling circle replication.

16. The method of claim 15, wherein the method further comprises the step of:
   (VI) sequencing the asymmetric closed-ended double stranded nucleic acid template or nanoball complexes using a sequencing primer and a polymerase.

17. The method of claim 16, wherein step (V) (ii) and step (VI) are can be combined together into a single step.

18. The method of claim 17, wherein step (V) (ii) and step (VI) are carried out in a well of an automated sequencing platform.

19. A method of sequencing tagmented DNA comprising complementary hairpin loops, comprising:
- (I) generating tagmented DNA comprising complementary hairpin loops at the 5' ends of each strand, wherein the hairpin loops comprise a base paired transposase recognition sequence, and wherein there is a gap of single stranded sequence between the 5' ends and the 3' ends of the tagmented DNA;
- (II) forming two extended strands of tagmented DNA comprising a transposase recognition sequence and complementary transposase recognition sequence at 5' and 3' ends of each extended strand of tagmented DNA by using a polymerase;
- (III) separating the extended strands of tagmented DNA and rehybridizing the transposase recognition sequences and complementary transposase recognition sequences at the ends of each of the extended strands of tagmented DNA to form to complementary hairpin loops; and
- (IV) sequencing the extended strand of tagmented DNA comprising complementary hairpin loops by using a sequencing polymerase.

20. The method of claim 19, wherein step (IV) is carried out in a well of an automated sequencing platform.

21. The method of claim 19, wherein prior to sequencing of step (IV):
- (III') generating nanoball complexes comprising polycistronic amplified extended strands of tagmented DNA.

* * * * *

UNITED STATES PATENT AND TRADEMARK OFFICE
CERTIFICATE OF CORRECTION

| | | |
|---|---|---|
| PATENT NO. | : 12,410,426 B2 | Page 1 of 1 |
| APPLICATION NO. | : 17/600046 | |
| DATED | : September 9, 2025 | |
| INVENTOR(S) | : Niall Anthony Gormley | |

It is certified that error appears in the above-identified patent and that said Letters Patent is hereby corrected as shown below:

In the Claims

In Column 18, Line 64, in Claim 17, delete "are can be" and insert -- are --.

Signed and Sealed this
Thirtieth Day of December, 2025

John A. Squires
*Director of the United States Patent and Trademark Office*